(12) United States Patent
Ekwall

(10) Patent No.: US 6,314,323 B1
(45) Date of Patent: Nov. 6, 2001

(54) HEART STIMULATOR DETERMINING CARDIAC OUTPUT, BY MEASURING THE SYSTOLIC PRESSURE, FOR CONTROLLING THE STIMULATION

(75) Inventor: Christer Ekwall, Spånga (SE)

(73) Assignee: Pacesetter AB, Järfälla (SE)

( * ) Notice: Subject to any disclaimer, the term of this patent is extended or adjusted under 35 U.S.C. 154(b) by 0 days.

(21) Appl. No.: 09/582,895

(22) PCT Filed: Jan. 7, 1999

(86) PCT No.: PCT/SE99/00007

§ 371 Date: Jul. 6, 2000

§ 102(e) Date: Jul. 6, 2000

(87) PCT Pub. No.: WO99/34863

PCT Pub. Date: Jul. 15, 1999

(30) Foreign Application Priority Data

Jan. 9, 1998 (SE) .................................................. 9800040

(51) Int. Cl.[7] ...................................................... A61N 1/36
(52) U.S. Cl. .......................... 607/23; 600/513; 600/526; 607/24
(58) Field of Search .................................. 600/513, 519, 600/526; 607/9, 23, 24

(56) References Cited

U.S. PATENT DOCUMENTS

| 4,566,456 | * | 1/1986 | Koning et al. | ............. 128/419 |
|---|---|---|---|---|
| 5,156,147 | | 10/1992 | Warren et al. . | |
| 5,183,051 | | 2/1993 | Kraidin et al. . | |
| 5,213,098 | * | 5/1993 | Bennett et al. | ............. 128/419 |
| 5,265,615 | | 11/1993 | Frank et al. . | |
| 5,324,326 | | 6/1994 | Lubin . | |

OTHER PUBLICATIONS

Thesis Dissertation "Korrelation zwischen Schlagvolumen und abgeleiteten Druckparametern des rechten Herzens—Eine tiereperimentelle Studie," K. Rohrbach, Ludwig-–Maximilians–Universität, Munich, Germany, 1991.

* cited by examiner

Primary Examiner—Jeffrey R. Jastrzab
Assistant Examiner—Frances P. Oropeza
(74) Attorney, Agent, or Firm—Schiff Hardin & Waite

(57) ABSTRACT

A heart stimulator has a circuit for determining cardiac output and for producing a control signal corresponding to the determined cardiac output, and a controller for controlling cardiac stimulation dependent on the control signal. The circuit for determining cardiac output includes a pressure sensor which measures pressure in the right ventricle and which generates an electrical pressure signal corresponding to the measured pressure, and an integrator supplied with the pressure signal which integrates the pressure signal between a start time and stop time to produce an integration result corresponding to the cardiac output, which is used to form the control signal. The pressure signal is bandpass filtered during a systolic phase to identify opening of a valve at the right ventricle as the start time, and to identify closing of the valve as the stop time.

12 Claims, 4 Drawing Sheets

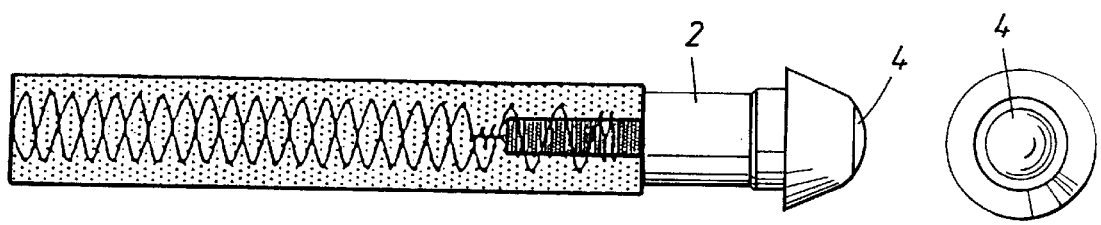
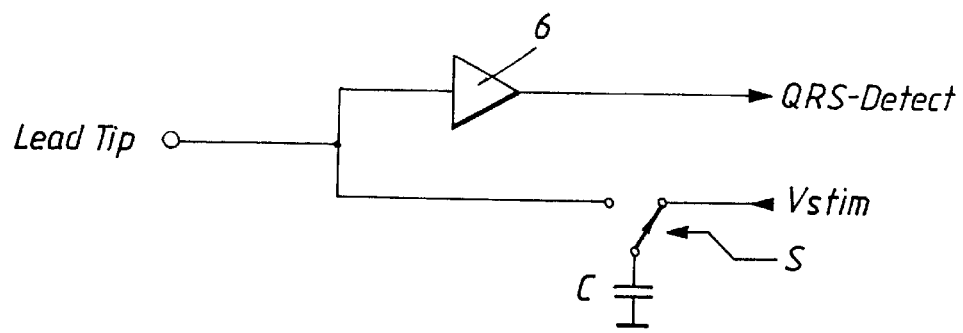

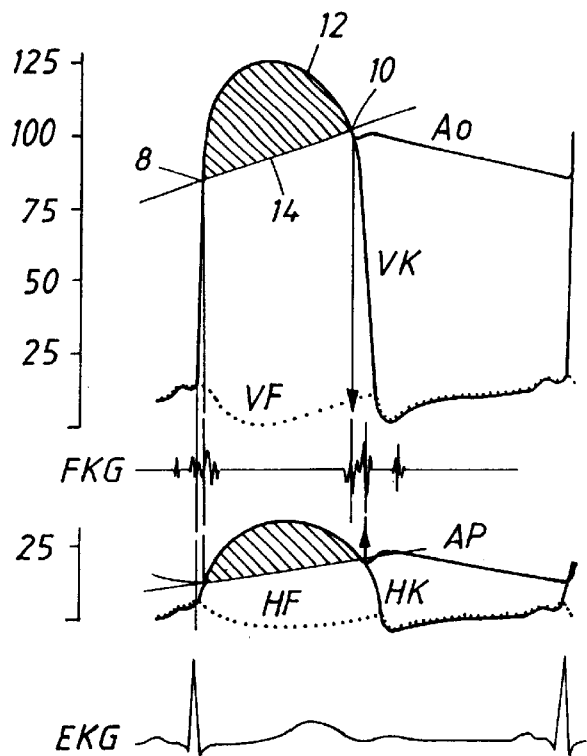
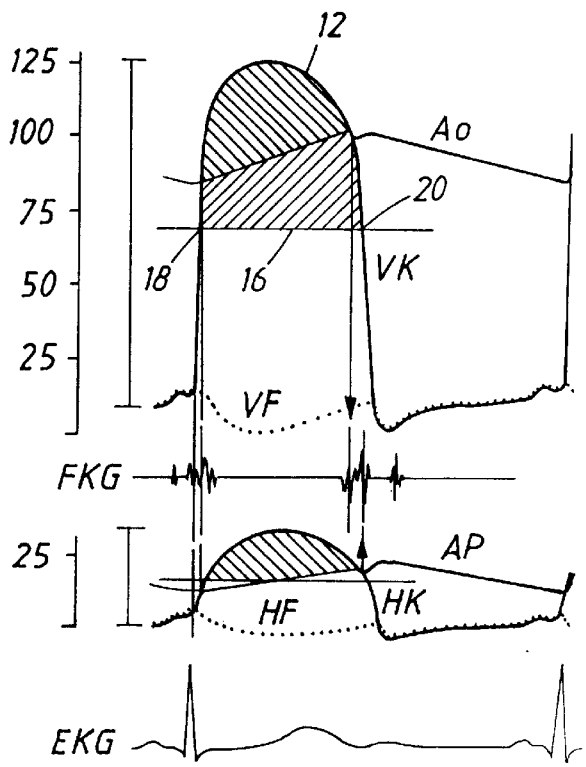

HEART STIMULATOR DETERMINING CARDIAC OUTPUT, BY MEASURING THE SYSTOLIC PRESSURE, FOR CONTROLLING THE STIMULATION

BACKGROUND OF THE INVENTION

1. Field of the Invention

The present invention relates to a heart stimulator for electrical stimulation of the heart of the type having means for determining cardiac output and control means for controlling the stimulation in response to the determined cardiac output, and wherein cardiac output determining means includes means for measuring the pressure inside the right ventricle and producing a corresponding pressure signal, and means for producing from the pressure signal a control signal related to the cardiac output and supplying the control signal to the control means for controlling the delivered stimulation according to the control signal.

2. Description of the Prior Art

Several other manners of automatic adaption of pacemaker stimulation algorithms and parameters are also known. A common shortcoming to all these prior concepts is that no really appropriate criteria have been found for the algorithm and parameter optimization. Thus attempts have been made to e.g. optimize the AV-delay based on an assumed algorithmic relation between cardiac rate or cardiac activity and an optimal AV-delay. However, the results have been unsatisfactory.

Because of the wide variety of conditions affecting the needs of the patient, such as mental onset, nutrition, time of the day and season, diseases and individual peculiarities, it is not likely that an algorithmic relation will ever come close to the real situation. A system of this kind is unlikely to be effective unless the effectiveness can be measured and used as feedback in a stimulation control. Today pacemaker parameters are normally adjusted depending on diagnosis and the experience of the medical personnel.

The above mentioned U.S. Pat. No. 5,156,147 describes a rate adaptive pacemaker having a variable rate cardiac stimulating pulse generator and a sensor for monitoring some physiologic parameter for adjusting the pulse generator stimulation rate to meet physiologic demands. In addition thereto a hemodynamic sensor is operative to provide an output signal representing the pumping performance of the heart in response to the pacing stimulation. The hemodynamic monitoring sensor may measure the right ventricular pressure, and it is mentioned that the hemodynamic parameter used for controlling the pacing output is determined from the measured pressure signal.

The above subject is achieved in accordance with the principle of the present invention in a heart stimulator having a circuit for determining cardiac output and for producing a control signal corresponding to the cardiac output, a controller for controlling cardiac stimulation dependent on the control signal, and wherein the cardiac output determining circuit includes a pressure sensor which measures pressure in the right ventricle and which generates an electrical signal to corresponding to the measured pressure, an integrator supplied with the pressure signal which integrates the pressure signal between a start time and a stop time to produce an integration result, corresponding to the cardiac output, for use as the control signal, and a bandpass filter connected to the integrator and to the pressure sensor for filtering the pressure signal during a systolic phase to identify opening of a valve at the right ventricle as the aforementioned start time for the integration and to identify a closing of this valve as the aforementioned stop time.

Also U.S. Pat. No. 5,183,051 discloses a method for continuously determining cardiac output from measured arterial blood pressure data. Blood pressure is measured non-invasively or minimally invasively and the stroke volume is determined from the stroke area under the pulse pressure curve between the start of the systolic phase and the dicrotic notch, said stroke area being corrected for any surface portions related to reflected pressure waves.

The methods of determining cardiac output according to the two last mentioned publications are used for diagnostic purposes. Nothing is mentioned about using cardiac output as a parameter for controlling a heart stimulator.

The article K. Rohrbach, Ludwig-Maximilians-Universitat Munchen 1991, "Korrelation zwischen Schlagvolumen und abgeleiteten Druckparametern des rechten Herzens—Eine tierexperimentelle Studie-" discloses different methods of determining the stroke volume from a pressure signal obtained in the right ventricle of a pig. According to one method in this thesis is the pressure signal integrated during systole.

SUMMARY OF THE INVENTION

An object of the present invention is to provide a simple arrangement for determining cardiac output as a measure of the effectiveness of the stimulation administered by a heart stimulator, and to use the determined cardiac output in a feedback procedure for adapting the stimulation as needed.

The above object is achieved in accordance with the principles of the present invention in a heart stimulator having a circuit for determining cardiac output and for producing a control signal corresponding to the cardiac output, a controller for controlling cardiac stimulation dependent on the control signal, and wherein the cardiac output determining circuit includes a pressure sensor which measures pressure in the right ventricle and which generates an electrical signal corresponding to the measured pressure, an integrator supplied with the pressure signal which integrates the pressure signal between a start time and a stop time tp produce an integration result, corresponding to the cardiac output, for use as the control signal, and a bandpass filter connected to the integrator and to the pressure sensor for filtering the pressure signal during a systolic phase to identify opening of a valve at the right ventricle as the aforementioned start time for the integration, and to identify a closing of this valve as the aforementioned stop time.

With the heart stimulator according to the invention it is possible in a simple and reliable way to adjust algorithms and one or more stimulation parameters dynamically in response to environmental and demand changes to maintain an optimum cardiac output. Examples of parameters which can be adjusted in such a feedback procedure are AV-delay, stimulation rate, refractory period, stimulation pulse energy, duration, and amplitude.

In an embodiment of the heart stimulator according to the invention cardiac output determining circuit measures the cardiac output on a beat to beat basis. It is then possible to calculate energy effectiveness per beat and hence energy consumption over time for a certain cardiac output. This is of vital importance in a heart stimulator since it is essential not to stress the heart and not to use more energy than needed in a certain situation.

According to another embodiment of the heart stimulator of the invention a sample and hold circuit is connected to the pressure sensor to hold the measured pressure value at the ventricle outflow valve opening, the integrator being controlled by the sample and hold circuit to continue integration as long as the measured systolic pressure is higher than the held valve opening pressure value. This is a practical way of defining the limits for the integration. The determination of these limits are not too critical, since the integrated area has the character of a relative measure and not an absolute one. Thus in practice a change of an input parameter is performed and the corresponding change of the integrated area, representing cardiac output, is observed, and with the aid of this information the next change of the input parameter in order to reach an optimum cardiac output is determined.

In another embodiment of the heart stimulator of the invention, the integrator is adapted to determine, as a measure of cardiac output, the magnitude of an area in the pressure versus time plane limited by the measured ventricular pressure curve as a function of time from ventricle outflow valve opening to valve closure and a straight line between the measured pressure values at ventricle outflow valve opening and closure. The pressure difference between the right ventricle and the pulmonary artery is the driving force accelerating blood out of the ventricle through the opened valve and the speed of blood flow is determined by this pressure difference and by the blood's density. Thus, from a theoretical point of view, the ventricle over pulmonary artery pressure difference is the relevant quantity to be integrated for determining the volume output per beat or cardiac output. During the ejection phase, however, the exact value of the pulmonary artery pressure cannot be measured from inside the ventricle. The pressure at the beginning of the ejection phase and at the end thereof can, however, be measured and the pulmonary artery constitutes an elastic system and the pressure is increasing approximately linearly with the enclosed volume. Consequently a straight line between the pressure at valve opening and the pressure at valve closure is a good approximate average value of the aortic pressure built up.

In a further embodiment of the heart stimulator of the invention the integrator is adapted to determine, as a measure of cardiac output, the magnitude of the area in the pressure versus time plane below the measured ventricular pressure curve and above a selected constant threshold level below the measured ventricular pressure, the integrator being controlled to start the integration as soon as the measured ventricular pressure exceeds said threshold level and stop the integration when the measured pressure drops below the threshold level. This is a simplified embodiment of the heart stimulator according to the invention with reduced complexity of electric circuitry, memory means and used algorithms, in which yet normally a good estimate of the cardiac output is obtained for controlling purposes. Since the pressure is steeply rising prior to valve opening and steeply falling after valve closure, using a constant level for determining start and end points of the integration will not significantly shift these points from actual valve opening and closure points, and provided that the threshold level is not changed relative to the pressure at valve opening from one beat to the next one, the difference between the measured cardiac output and actual cardiac output will be approximately constant. This difference between measured and actual cardiac output values can then be eliminated by forming the difference between consecutive measured values.

DESCRIPTION OF THE DRAWINGS

FIG. 1A shows a longitudinal view and FIG. 1B shows an end view of the end portion of a ventricular lead suitable for use with the heart stimulator according to the invention.

FIG. 2 is a principal diagram of an input circuitry for stimulation and QRS-detection of the heart stimulator according to the invention.

FIG. 3 shows pressures measured in different parts of the heart and the aortic and pulmonary artery pressures as a function of time as well as phonocardio- and electrocardiograms for illustrating one method of determining cardiac output in the stimulator according to the invention.

FIGS. 4–6 show the same pressure curves and phono- and electrocardiograms for illustrating alternative methods of determining the cardiac output in the heart stimulator according to the invention.

DESCRIPTION OF THE PREFERRED EMBODIMENTS

Figure 5:
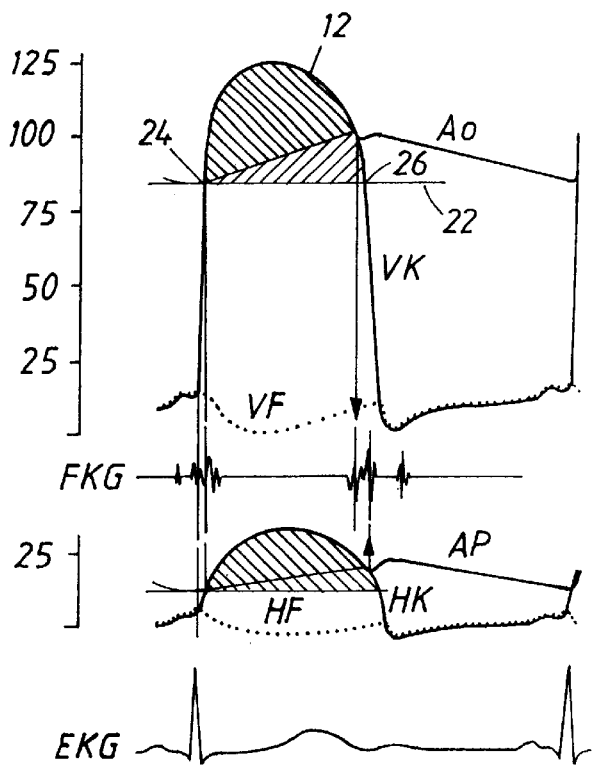

In the heart stimulator according to the invention cardiac output is determined as the time integral of the pressure in the ventricle during the systolic phase of the heart. The pressure is preferably measured by a pressure sensor 2 positioned behind the tip of a ventricular electrode lead intended to be used with a heart stimulator according to the invention, see FIGS. 1A and 1B. The lead tip 4 is electrically connected to the heart stimulator for conducting stimulation impulses to heart tissue and, in most applications, also for sensing electrical activity arising from heart contraction. The pressure sensor 2 is preferably a piezoelectric sensor also connected to the heart stimulator for delivering a pressure signal representing the sensed pressure.

FIG. 2 shows the input circuitry of a heart stimulator according to the invention. A stimulation capacitor C is charged to a predetermined stimulation voltage $V_{stim}$ from a battery in the heart stimulator (not shown in the figure), the switch S then being in the position shown in FIG. 2. A stimulation pulse can thereafter be delivered from the capacitor C through the electrode lead to the tip 4 by moving the switch S to its second position for connecting the capacitor C to the lead.

As mentioned above the lead tip 4 is also used for sensing electrical heart activity and the sensed signals are supplied to a QRS-detector 6 for QRS-detection for use in the control of the pacemaker.

The following description will be made with respect to the left ventricle. However, as the vascular system is a closed system the blood volume flowing in different parts of the system will be essentially the same and therefore the description is also applicable to the right ventricle. In steady state left and right ventricular cardiac output will be equal. Temporary variations will result in a redistribution of pressures and a new steady state situation will rapidly emerge.

FIG. 3 shows measured pressure curves during a cardiac cycle. During systole the pressure inside the ventricle is rapidly increasing. At a certain level 8 the pressure exceeds the pressure in the aorta and the aortic valve opens. This is the start of the ejection phase in which blood is driven out of the ventricle into the aorta. The pressure difference between the ventricle and the aorta is the driving force accelerating blood out of the ventricle through the open valve. The speed of the blood flow is determined by this pressure difference and the density of the blood. The area of the valve opening is substantially constant from beat to beat and the volume output per beat or cardiac output is found to be proportional to the time integral of the pressure difference over the ejection time from valve opening 8 to valve closure 10 in FIG. 3.

From a theoretical point of view the difference between the pressure in the ventricle and the aortic pressure is thus the pertinent quantity to be integrated. During the ejection phase, however, the exact value of the aortic pressure cannot be measured from the inside of the ventricle, but only at the start 8 and at the end 10 of the systolic phase. The aorta constitutes an elastic system and the pressure is increasing approximately linearly with the enclosed volume. A straight line between the valve opening 8 and the valve closure 10 therefore forms a good approximation of the build-up of the aortic pressure. This has been verified by comparative measurements of cardiac output by a flowmeter and by the measurements described above.

Thus, in one embodiment of the heart stimulator according to the invention, cardiac output is determined by integration of the surface delimited by the pressure curve 12 and the assumed linearly varying aortic pressure 14.

To simplify circuitries, memories, and algorithms needed for determining cardiac output as described above modifications of the described procedure are possible.

As noted above the pressure rise and fall prior to valve opening and after valve closure respectively are steep. During this rise and fall the elastic effect from the aorta has no leveling or smoothing influence on the variation of the pressure, and because of the steepness of the pressure curve a constant level, represented by the straight line 16 in FIG. 4, can be used for defining the start and end points 18, 20 of the integration. Using the intersection points between this straight line 16 and the pressure curve 12 as start and end points for the integration instead of the intersection points between e.g. the inclined line 14 and the pressure curve 12 as in FIG. 3 will only result in minor shifts of the start and end points. If the level of the line 16 relative to the pressure at the valve opening is the same from one beat to the next one, the difference between the actual cardiac output and the measured cardiac output will be approximately constant and have practically no influence on a relative measurement of cardiac output which is sufficient for the control of the heart stimulator according to the invention.

As such a reference level for the integration half the peak systolic pressure from a base line can be chosen.

Figure 6:
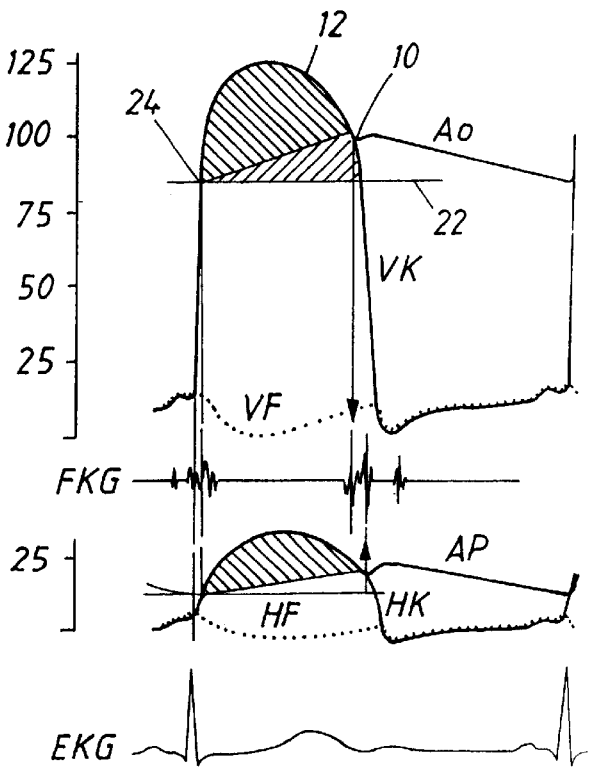

In another alternative embodiment of the heart stimulator according to the invention the pressure inside the ventricle is monitored by a sample and hold circuit. The pressure measured at the point of valve opening is then Hold and the integration is started and continued as long as the systolic pressure remains higher than the hold value or till valve closure. These two possibilities are illustrated in FIGS. 5 and 6 respectively. Thus a horizontal straight line 22 through the pressure at valve opening 24 forms the reference for the integration. In the embodiment illustrated in FIG. 5 the integration is stopped at the intersection point 26 between the falling flank of the pressure curve 12 and the reference line 22 and in the embodiment illustrated by FIG. 6 the integration is stopped at valve closure 10 as also illustrated in FIG. 3.

The embodiment incorporating sample and hold circuits will be described in greater detail below with reference to FIGS. 7 and 8.

In FIGS. 3–6 the discussed pressure curve 12, which continues as a curve VK in the second half of the shown cardiac cycle, represents the pressure measured in the left ventricle. The curve Ao shows the aortic pressure and the dotted curve VF illustrates measured pressure in the left atrium.

FKG is a phono cardiogram which shows increased noise at valve opening and valve closure. This increased noise can be detected by an acoustic sensor and used for detecting valve opening and closure.

The pressure curve HK represents the pressure in the right ventricle and this curve can be used for determining cardiac output in an analogous way as the pressure curve 12. The curve AP represents measured pressure in the pulmonary artery and the dotted curve HF the pressure in the right atrium. EKG denotes an electrocardiogram.

By a pressure sensor with a reasonably high frequency response positioned in the ventricle it is possible to detect pressure artifacts resulting from the acceleration and deceleration of fluid at valve opening and closing. These pressure artifacts appear as damped periodic oscillations, the frequency of which is determined by the elastic property of the system formed by e.g. aorta, or pulmonary artery, and ventricle, and the mass density of the fluid. By using a narrow bandpass filter valve opening and closure can be detected from these oscillations in the pressure signal.

Figure 7:
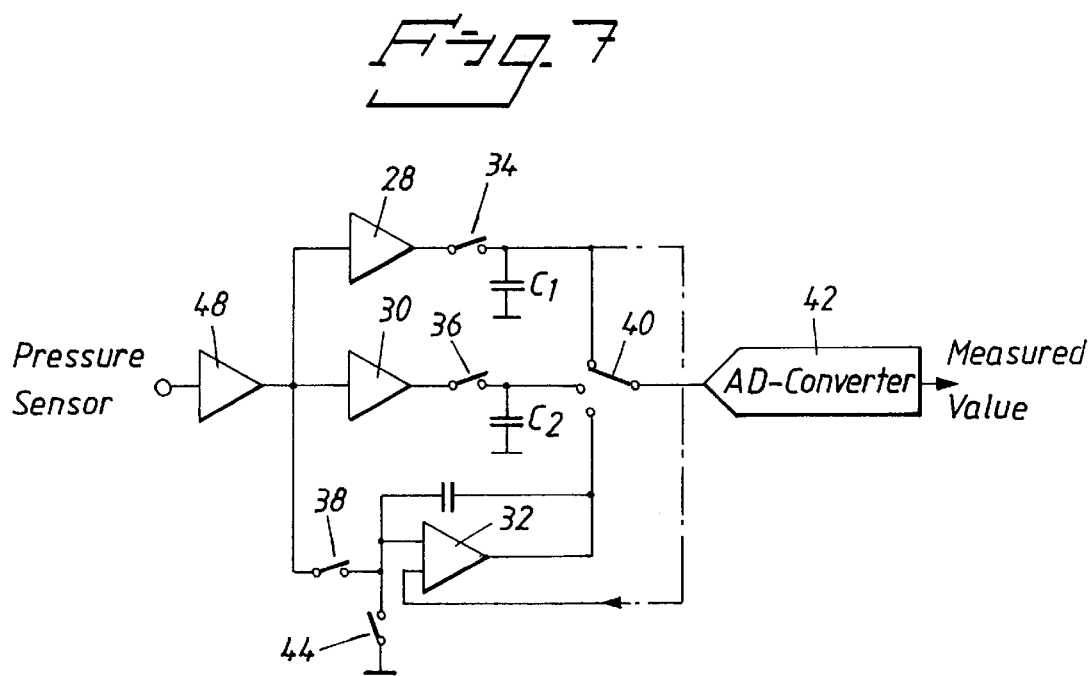
FIG. 7 shows a first embodiment of a cardiac output measuring circuitry of the heart stimulator according to the invention.

A first embodiment of the circuitry for determining cardiac output in the heart stimulator according to the invention is shown in FIG. 7. This circuit includes two sample and hold circuits 28, 30, and an integrator 32.

At valve opening the integration is started and the first sample and hold circuit 28 is brought into Hold position by the switch 34. In this way the end diastolic pressured is stored on the hold capacitor $C_1$ of this circuit.

At valve closure the integration is stopped and the second sample and hold circuit 30 is brought into Hold position with the aid of the switch 36. The end systolic pressure is then stored on the hold capacitor $C_2$ of this circuit.

Start and stop of the integration is controlled by the switch 38.

In the embodiment shown in FIG. 7 the end diastolic pressure is supplied to the integrator 32 as integral reference.

By a multiplexor 40 the diastolic and systolic pressures as well as integrated pressure values are supplied to an AD-converter 42 for digitization and transfer to the heart stimulator controller.

To make the integrator 32 ready for the next measurement it is reset by closure of the switch 44.

In this embodiment cardiac output thus will be calculated according to the formula Cardiac Output=Pressure Integral–(End Systolic Pressure–End Diastolic Pressure)×time/2 as explained in connection with FIG. 3.

Figure 8:
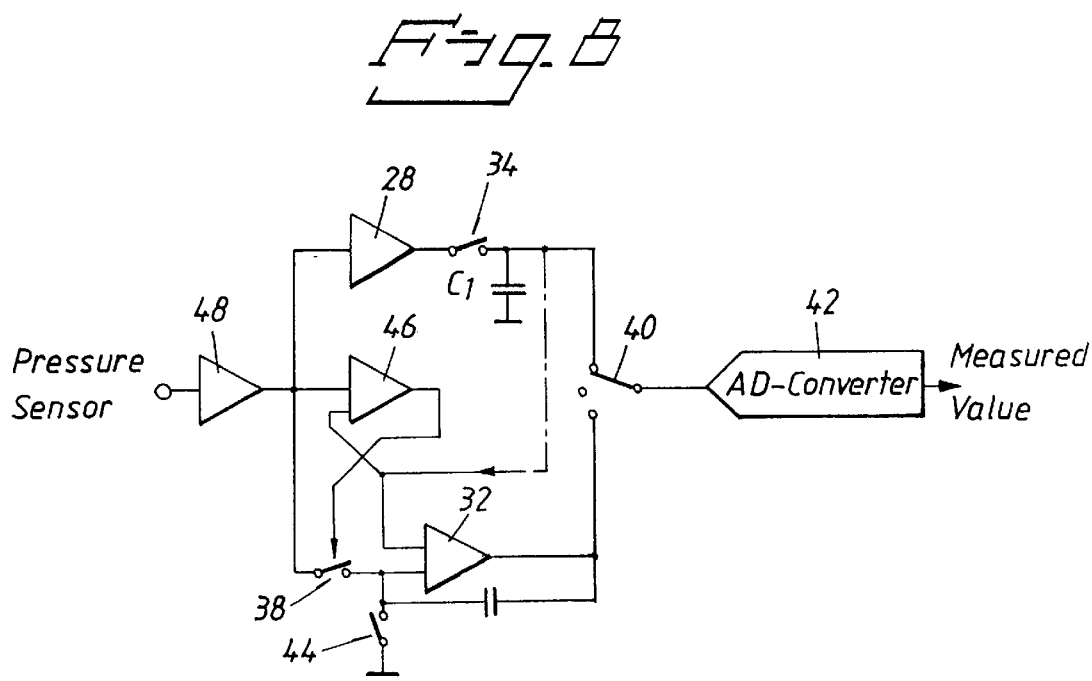
FIG. 8 shows a second embodiment of the circuitry for determining cardiac output from the pressure signal in the heart stimulator according to the invention.

FIG. 8 shows an alternative embodiment of the circuitry in which the second sample and hold circuit is replaced by a comparator circuit 46. By the first sample and hold circuit 28 the end diastolic pressure is stored on the capacitor $C_1$. The stored end diastolic pressure is used as an integral reference and is supplied to the comparator 46 and the integrator 32. In the comparator 46 the sensed pressure signal, amplified in the pressure amplifier 48 is compared with the reference. As the pressure signal exceeds the integral reference value the comparator 46 delivers an output signal closing the switch 38 for starting the integration of the pressure signal. The integration is stopped when the pressure signal drops below the integral reference, i.e. the stored end diastolic pressure.

The integral reference value is also fed to the integrator 32 such that the area delimited by the sensed pressure curve and the end diastolic pressure in the pressure versus time plane is determined by the integrator 32.

Similarly as in the embodiment in FIG. 3 an integrator reset switch 44 is provided and a multiplexor 40 for supplying the end diastolic pressure and the integration value to the AD-converter 42 for digitization and transfer to the pacemaker controller.

Valve opening and closing can be detected by filtering the pressure signal as described above and the detected opening and closing events are controlling the switches of the circuitry in FIGS. 7 and 8. As mentioned above a pressure sensor, preferably of a piezoelectric type, is used. However, any other type of pressure sensor having a sufficiently high frequency range response, typically 200–500 Hz, can be used.

Alternatively heart sound from the valves can be used for determining valve opening and closure. As appears from the phono cardiograms in FIGS. 3–6 there is a characteristic increase in the recorded sounds at valve opening and closure.

As still another alternative valve opening and closure can be determined from recorded electrocardiograms. The electrocardiograms can be recorded by the ordinary electrode lead used for stimulation or by a separate lead.

Yet another alternative for determining valve opening, and consequently the starting point for the integration, in case of pacemaker stimulation, consists in adding an appropriate delay, typically 40 msec, from the timing position for a delivered stimulation pulse.

Cardiac output can also be determined from a measured AC-impedance signal. The AC-impedance signal is varying with time in a similar way as the pressure signal. The volume of blood contained in the heart is reflected in the value of the AC-impedance. More blood contained in the heart results in a lower impedance. For using the impedance as a measure of the pressure, it is necessary that the impedance is measured locally in the ventricle, i.e. by a bipolar electrode.

For determining the impedance as a measure of the pressure a separate measurement catheter can be used, as well.

With the heart stimulator according to the invention the possibilities for satisfying the patient's need with a minimum energy consumption are improved.

Energy consumption per heartbeat is fairly constant if other conditions for the patient remain essentially unchanged. Factors affecting energy consumption are hypertension and heart onset caused by the autonomous nerve system and hormone release. Both these factors increase energy consumption per heartbeat. For a patient suffering from hypertension the heart has to pump blood against an increased pressure when opening the outlet aortic or pulmonary valve. Heart onset is related to the metabolic demand, e.g. due to workload.

Metabolic demand is setting the level of the peripheral vascular resistance which can preferably be determined from the end diastolic pressure, i.e. the aortic pressure at aortic valve opening. As the peripheral vascular resistance increases the pressure drops more rapidly and a lower end diastolic pressure results. Peripheral vascular resistance can alternatively be determined from venous blood return to the heart or indirectly by means of sensors. Examples of such sensors are body activity sensors, based on body movements, or muscular sound waves or metabolic sensors sensing oxygen or carbon dioxide saturation, pH value or blood temperature. Utilizing a pressure sensor is, however, to prefer, since combined monitoring of different physiological parameters is then possible by one single sensor. Thus metabolic need can be determined from the end diastolic pressure, heart inability can be detected by sensed ischemic episodes, the heart can be monitored by sensed normal spontaneous systolic, stimulation capture can be monitored by sensed evoked systolic response and cardiac output can be monitored by determining the systolic pressure integral, as described above. Such a pressure sensing system will closely mimic the natural system of the body.

From a signal representing the metabolic demand measured according to one of the techniques mentioned above, with possible compensation for pathological factors, such as ischemia or hypertension, a desired cardiac output control value can be determined by a suitable algorithm or from tables. The actual cardiac output is determined from the systolic pressure integral as described above and stimulation parameters of the heart stimulator according to the invention are changed in small steps followed by evaluation of the resulting cardiac output after each change. If cardiac output is increased the new parameter value will replace the old one, and if cardiac output decreases, no parametric change is performed.

As an example of this way of controlling the heart stimulator a single parameter adjusting system in the form of a rate adaption system will be described.

With a patient at rest the stimulation rate is decreased in small steps till a heart rate is reached which results in the desired cardiac output. If the workload is increased the desired cardiac output is increased, too. The stimulation rate is increased in steps as long as the resulting cardiac output is increased. At a certain rate limit venous blood return will not be sufficient for refilling the heart between consecutive systoles, and further rate increase will then actually decrease cardiac output. At this point the heart stimulator according to the invention will automatically stop further rate increase and keep the stimulation rate at the value which gives a maximum cardiac output.

The adjustment of the stimulation can also include changing stimulation parameters other than the stimulation rate, like stimulation pulse amplitude, duration and shape of the pulse. At the site of an implanted stimulation lead different conduction patterns can arise for different stimulation energy levels. Thus e.g. a conduction barrier can exist for energies below a certain threshold. In such a case the propagating depolarization wave must find another way around the area in question with an associated delay in the conduction pattern. Such a delay will also affect the time progress of the contraction pattern and reduce cardiac output. This phenomenon occurs more easily if the implanted lead does not have an optimal location. A sufficiently high stimulation energy will stimulate a larger tissue volume around the lead and can in this way "compensate" for the less suitable positioning of the lead.

Stimulating leads are implanted into the right ventricle. From a site in the right ventricle a minimum stimulation energy is needed to overcome delay across the septum and to match left and right ventricle contraction patterns. For a patient having left bundle branch block it can be difficult to reach the left ventricle from the right ventricle, anyhow a higher energy can be required.

In the heart stimulator according to the invention a single parameter, or a combination of parameters, can be optimized, each parameter then being adjusted and evaluated in a sequence of optimization. Thus, e.g. the AV-delay in a two-chamber system can be varied to reach an optimum cardiac output per beat and the heart rate is accordingly decreased to maintain the desired cardiac output.

The time delay after a delivered stimulation pulse can be in the range of 0–100 msec.

Although modifications and changes may be suggested by those skilled in the art, it is the intention of the inventor to embody within the patent warranted hereon all changes and modifications as reasonably and properly come within the scope of his contribution to the art.

I claim:

1. A heart stimulator comprising:

a circuit for determining cardiac output and for producing a control signal corresponding to said cardiac output;

a controller for controlling cardiac stimulation dependent on said control signal; and said circuit including a pressure sensor adapted to sense pressure in a right ventricle and to generate an electrical pressure signal corresponding to the sensed pressure, an integrator supplied with said pressure signal which integrates said pressure signal between a start time and a stop time to produce an integration result, corresponding to said cardiac output, forming said control signal, and wherein said pressure signal is bandpass filtered during a systolic phase to identify opening of a valve at said right ventricle as said start time and closing of said valve as said stop time.

2. A heart stimulator as claimed in claim 1 wherein said circuit determines said cardiac output on a beat-to-beat basis.

3. A heart stimulator as claimed in claim 1 wherein said circuit determines said cardiac output as an average value over a plurality of heartbeats.

4. A heart stimulator as claimed in claim 1 further comprising a lead having an electrode tip for conducting stimulation pulses to heart tissue and for sensing electrical heart activity, said lead also carrying said pressure sensor.

5. A heart stimulator as claimed in claim 4 wherein said pressure sensor comprises a piezoelectric pressure sensor disposed behind said electrode tip.

6. A heart stimulator as claimed in claim 1 wherein said integrator determines, as a measure of said cardiac output, a magnitude in an area of a pressure versus time plane limited by a curve represented by said pressure signal as a function of time between said start time and said stop time, and a straight line proceeding between respective values of said pressure signal at said start time and said stop time.

7. A heart stimulator as claimed in claim 1 further comprising a sensor for determining a metabolic need of a patient and for generating a metabolic need signal corresponding said metabolic need, and a comparator for comparing said metabolic need signal with said integration result, to obtain a comparison result, said comparison result forming said control signal.

8. A heart stimulator as claimed in claim 7 wherein said metabolic need sensor comprises a flow sensor adapted to measure venous blood return to the heart.

9. A heart stimulator as claimed in claim 7 wherein said metabolic need sensor comprises a further pressure sensor adapted to detect end diastolic pressure.

10. A heart stimulator as claimed in claim 7 wherein said metabolic need sensor comprises an activity sensor.

11. A heart stimulator as claimed in claim 7 wherein said metabolic need sensor comprises a sensor adapted to measure a blood parameter selected from the group consisting of blood oxygen saturation, blood carbon dioxide saturation, blood pH and blood temperature.

12. A heart stimulator as claimed in claim 1 comprising a stimulation pulse emitter for administering said stimulation, said stimulation pulse emitter having a stimulation rate, a stimulation pulse amplitude, a pulse duration and a pulse shape associated therewith, and wherein said control signal operates said stimulation pulse generator to adjust at least one of said parameters.

* * * * *